United States Patent
Lyu et al.

(10) Patent No.: US 7,718,278 B2
(45) Date of Patent: May 18, 2010

(54) ANTHRANCENE DERIVATIVE COMPOUND AND ORGANIC LIGHT-EMITTING DEVICE INCLUDING THE SAME

(75) Inventors: Yi-yeol Lyu, Yongin-si (KR); Jhun-mo Son, Yongin-si (KR); Das Rupasree Ragini, Yongin-si (KR); Byoung-ki Choi, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 396 days.

(21) Appl. No.: 11/832,791

(22) Filed: Aug. 2, 2007

(65) Prior Publication Data

US 2008/0122346 A1    May 29, 2008

(51) Int. Cl.
   *C07D 279/22*    (2006.01)
(52) U.S. Cl. ......................................... 428/690; 544/35
(58) Field of Classification Search ........................ None
   See application file for complete search history.

(56) References Cited

U.S. PATENT DOCUMENTS

| | | | |
|---|---|---|---|
| 4,356,429 A | 10/1982 | Tang | |
| 4,885,211 A | 12/1989 | Tang et al. | |
| 5,151,629 A | 9/1992 | VanSlyke | |

FOREIGN PATENT DOCUMENTS

JP         1999003782 A    6/1997

OTHER PUBLICATIONS

Jenekhe et. al., Macromolecules (2001), 34(21), p. 7315-7324.*
Advanced Material, 6, p. 677 (1994); Yoshiyiki Kuwabara, Hiromitsu Ogawa, Hiroshi Inada, Naoki Noma, and Yasuhiko Shirota.

* cited by examiner

*Primary Examiner*—D. Lawrence Tarazano
*Assistant Examiner*—Gregory Clark
(74) *Attorney, Agent, or Firm*—Cantor Colburn LLP

(57) ABSTRACT

Provided is an anthracene derivative compound represented by Formula 1 below and an organic light-emitting device using the same:

<Formula 1>

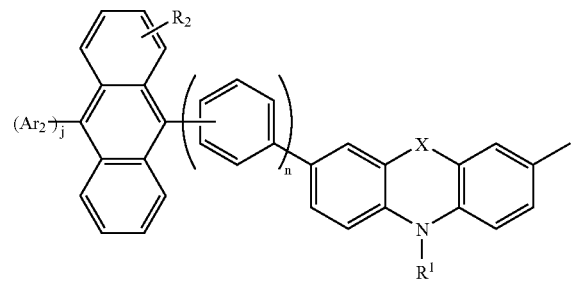

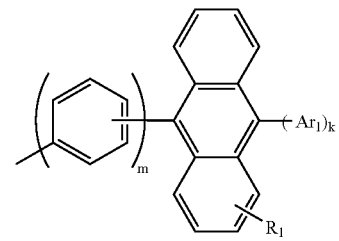

wherein $Ar_1$, $Ar_2$, $R_1$, $R_2$, $R'$, m, n, j, k, and X are as defined in the specification. The anthracene derivative compound is advantageously used in the production of an organic light-emitting device with better driving voltage, efficiency, and color purity.

10 Claims, 1 Drawing Sheet

FIG. 1A

| SECOND ELECTRODE |
|---|
| ELECTRON INJECTION LAYER |
| ELECTRON TRANSPORT LAYER |
| EMITTING LAYER |
| HOLE TRANSPORT LAYER |
| HOLE INJECTION LAYER |
| FIRST ELECTRODE |

FIG. 1B

| SECOND ELECTRODE |
|---|
| ELECTRON INJECTION LAYER |
| ELECTRON TRANSPORT LAYER |
| EMITTING LAYER |
| HOLE TRANSPORT LAYER |
| FIRST ELECTRODE |

FIG. 1C

| SECOND ELECTRODE |
|---|
| ELECTRON INJECTION LAYER |
| ELECTRON TRANSPORT LAYER |
| HOLE BLOCKING LAYER |
| EMITTING LAYER |
| HOLE TRANSPORT LAYER |
| HOLE INJECTION LAYER |
| FIRST ELECTRODE |

ANTHRANCENE DERIVATIVE COMPOUND AND ORGANIC LIGHT-EMITTING DEVICE INCLUDING THE SAME

CROSS-REFERENCE TO RELATED PATENT APPLICATION

This application claims priority to Korean Patent Application No. 10-2006-0119124, filed on Nov. 29, 2006, and all the benefits accruing therefrom under 35 U.S.C. §119, the content of which is incorporated herein by reference in its entirety.

BACKGROUND OF THE INVENTION

1. Field of the Invention

The present invention relates to an anthracene derivative compound and an organic light-emitting device (OLED) comprising the same. More specifically, the present invention relates to an anthracene derivative compound that has good electrical characteristics, and when applied to an OLED, can provide an excellent driving voltage, efficiency, and color purity.

2. Description of the Related Art

OLEDs are active emission display devices that emit light by recombination of electrons and holes in a thin layer (hereinafter referred to as "organic layer") formed of a fluorescent or phosphorescent organic compound when a current is supplied to the organic layer. The OLEDs have advantages such as lightness, simple constitutional elements, easy manufacturing process, superior image quality, and wide viewing angle. In addition, the OLEDs can advantageously create dynamic images, achieve high color purity, and have electrical properties suitable for portable electronic equipment due to low power consumption and low driving voltage.

Eastman Kodak Co. has developed an OLED with a multi-layered structure comprising an aluminum quinolinol complex layer and a triphenylamine derivative layer (U.S. Pat. No. 4,885,211), and an OLED comprising an organic light-emitting layer formed of a low molecular weight material capable of emitting light in a broad wavelength range from UV to infrared light (U.S. Pat. No. 5,151,629).

Light-emitting devices (LEDs) are self-emitting devices that have advantages such as a wide viewing angle, good contrast, and a rapid response time. LEDs are classified into inorganic light-emitting devices, which comprise an emitting layer formed of an inorganic compound, and OLEDs, which comprise an emitting layer formed of an organic compound. OLEDs display better brightness, driving voltage, and response speed characteristics and can produce polychromatic light, compared to inorganic light-emitting devices, and thus, extensive research into OLEDs has been conducted.

Generally, OLEDs have a stacked structure of an anode, an organic light-emitting layer, and a cathode. OLEDs may also have various structures such as anode/hole injection layer/hole transport layer/emitting layer/electron transport layer/electron injection layer/cathode or anode/hole injection layer/hole transport layer/emitting layer/hole blocking layer/electron transport layer/electron injection layer/cathode.

Materials used for OLEDs can be divided into vacuum-depositable materials and solution-coatable materials according to the organic layer manufacturing process. Vacuum-depositable materials advantageously have a vapor pressure of $10^{-6}$ torr or more at 500° C. or less, and may be low molecular weight materials having a molecular weight of 1,200 atomic mass units (amu) or less. Solution-coatable materials advantageously have solubility sufficient to form solutions, and generally comprise an aromatic or heterocyclic ring.

When manufacturing OLEDs using a vacuum deposition process, manufacturing costs may increase due to the use of a vacuum system, and it may be difficult to manufacture high-resolution pixels for natural color displays using a shadow mask. On the other hand, when manufacturing OLEDs using a solution coating process, such as inkjet printing, screen printing, spin coating, or the like, the manufacturing process is simple, manufacturing costs are low, and a relatively high resolution can be achieved compared to when using a shadow mask.

However, when using solution-coatable materials, the performance (for example, thermal stability, color purity, or the like) of light-emitting molecules is lowered compared to when using vacuum-depositable materials. Even though the light-emitting molecules of the solution-coatable materials have good performance, they provide problems when formed into an organic layer. For example, the materials gradually undergo crystallization and these crystals grow into a size that corresponds to a wavelength in the visible light regime, and thus, the grown crystals scatter visible light, thereby causing turbidity. In addition, defects such as pinholes, and the like may be formed in the organic layer, thereby causing device degradation.

Japanese Patent Laid-Open Publication No. 1999-003782 discloses a 2-naphthyl-substituted anthracene compound that can be used in an emitting layer or a hole injection layer. However, OLEDs comprising the anthracene compound are unsatisfactory in terms of driving voltage, brightness, efficiency, and color purity characteristics, and thus, there is room for improvement in conventional OLEDs.

SUMMARY OF THE INVENTION

In one embodiment, there is provided an anthracene derivative compound capable of improving the driving voltage, efficiency, and color purity characteristics of an OLED, and an OLED comprising the same.

According to an embodiment, there is provided an anthracene derivative compound represented by Formula 1 below:

<Formula 1>

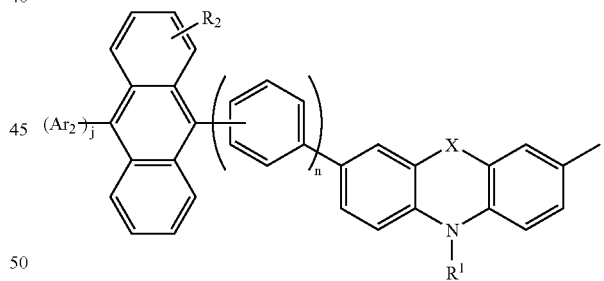

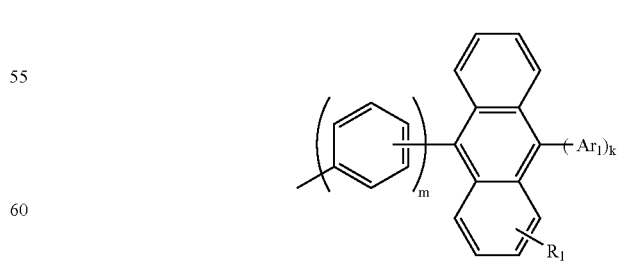

wherein $Ar_1$ and $Ar_2$ are each independently selected from the group consisting of a substituted or unsubstituted $C_5$-$C_{30}$ aryl group, a substituted or unsubstituted $C_1$-$C_{30}$ cycloaryl group, and a substituted or unsubstituted $C_6$-$C_{30}$ arylalkyl group; X is O,

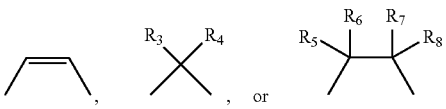

where $R_3$, $R_4$, $R_5$, $R_6$, $R_7$, and $R_8$ are each independently hydrogen or a substituted or unsubstituted $C_1$-$C_{12}$ alkyl group; n, m, j, and k are each independently 0 or 1; $R_1$ and $R_2$ are each independently selected from the group consisting of a hydrogen, a halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{20}$ aryl group, a substituted or unsubstituted $C_6$-$C_{20}$ arylalkyl group, and a substituted or unsubstituted $C_2$-$C_{20}$ heteroaryl group; and R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

Specifically, the anthracene derivative compound may be represented by Formula 2 below:

<Formula 2>

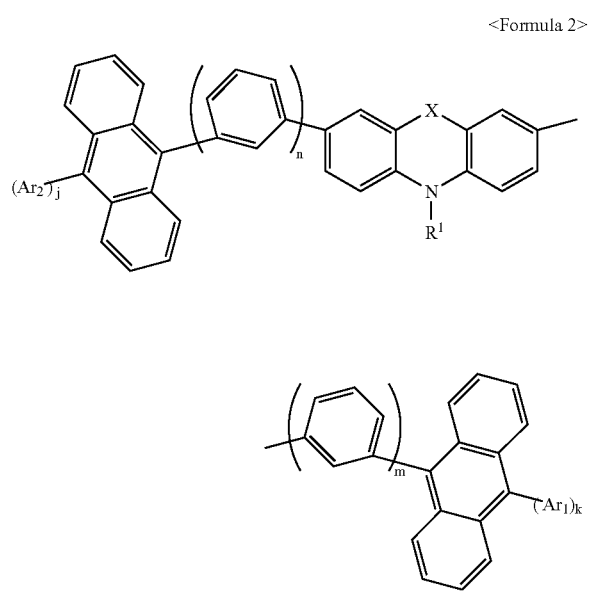

wherein $Ar_1$ and $Ar_2$ are each independently selected from the group consisting of a substituted or unsubstituted $C_5$-$C_{20}$ aryl group, a substituted or unsubstituted $C_1$-$C_{30}$ cycloaryl group, and a substituted or unsubstituted $C_6$-$C_{30}$ arylalkyl group; X is O,

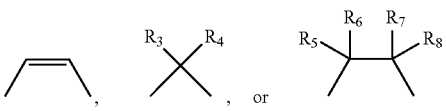

where $R_3$, $R_4$, $R_5$, $R_6$, $R_7$, and $R_8$ are each independently hydrogen or a substituted or unsubstituted $C_1$-$C_{12}$ alkyl group; n, m, j, and k are each independently 0 or 1; and R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

According to another embodiment, there is provided an OLED comprising: a first electrode; a second electrode; and at least one organic layer interposed between the first electrode and the second electrode, the organic layer comprising the above-described anthracene derivative compound.

The OLED comprising the anthracene derivative compound can show better driving voltage, efficiency, and color purity.

BRIEF DESCRIPTION OF THE DRAWINGS

The above and other features and advantages will become more apparent by describing in detail exemplary embodiments thereof with reference to the attached drawings in which:

FIG. 1A is a schematic view illustrating an OLED according to an embodiment;

FIG. 1B is a schematic view illustrating an OLED according to another embodiment; and FIG. 1C is a schematic view illustrating an OLED according to another embodiment.

DETAILED DESCRIPTION OF THE INVENTION

The invention is described more fully hereinafter with reference to the accompanying drawings, in which embodiments of the invention are shown. This invention, however, should not be construed as limited to the embodiments set forth herein. Rather, these embodiments are provided to convey the scope of the invention to those skilled in the art. In the drawings, the size and relative sizes of elements and regions may be exaggerated for clarity.

It will be understood that when an element or layer is referred to as being "on," "interposed," "disposed," or "between" another element or layer, it can be directly on, interposed, disposed, or between the other element or layer or intervening elements or layers may be present.

It will be understood that, although the terms first, second, third, and the like may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, first element, component, region, layer or section discussed below could be termed second element, component, region, layer or section without departing from the teachings of the present invention.

As used herein, the singular forms "a," "an" and "the" are intended to comprise the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Provided herein is an anthracene derivative compound represented by Formula 1 below:

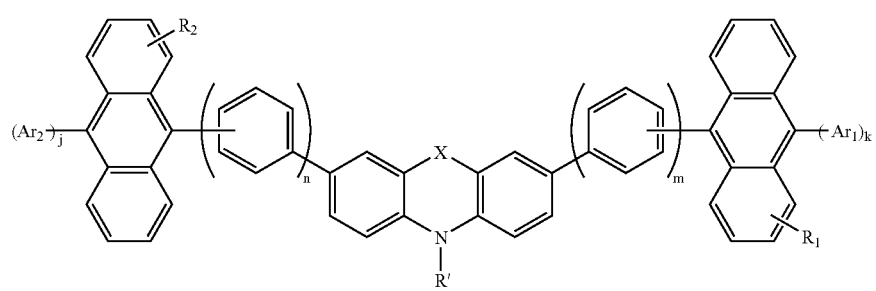

<Formula 1> wherein, $Ar_1$ and $Ar_2$ are each independently selected from the group consisting of a substituted or unsubstituted $C_5$-$C_{30}$ aryl group, a substituted or unsubstituted $C_1$-$C_{30}$ cycloaryl group, and a substituted or unsubstituted $C_6$-$C_{30}$ arylalkyl group; X is O,

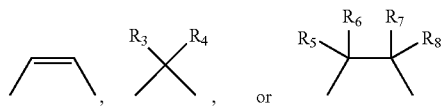

where $R_3$, $R_4$, $R_5$, $R_6$, $R_7$, and $R_8$ are each independently hydrogen or a substituted or unsubstituted $C_1$-$C_{12}$ alkyl group; n, m, j, and k are each independently 0 or 1; $R_1$ and $R_2$ are each independently selected from the group consisting of hydrogen, halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{20}$ aryl group, a substituted or unsubstituted $C_6$-$C_{20}$ arylalkyl group, and a substituted or unsubstituted $C_2$-$C_{20}$ heteroaryl group; and R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

When phenyl groups are incorporated as spacers, i.e., when n=1 and m=1, the phenylene moieties of the anthracene derivative compound of Formula 1 may be incorporated to form the meta-positions of the phenylene moieties. That is, the anthracene derivative compound of Formula 1 may be a compound represented by Formula 2 below:

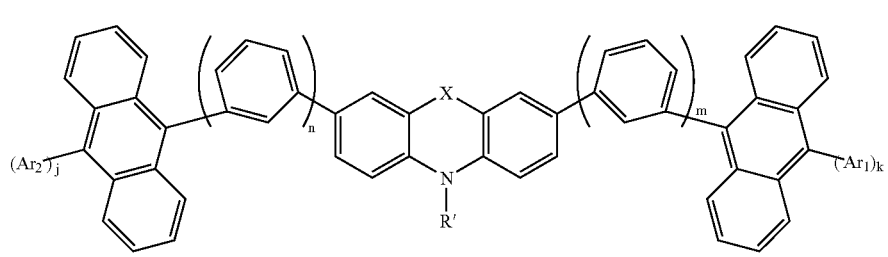

<Formula 2> wherein $Ar_1$ and $Ar_2$ are each independently selected from the group consisting of a substituted or unsubstituted $C_5$-$C_{20}$ aryl group, a substituted or unsubstituted $C_1$-$C_{30}$ cycloaryl group, and a substituted or unsubstituted $C_6$-$C_{30}$ arylalkyl group; X is O,

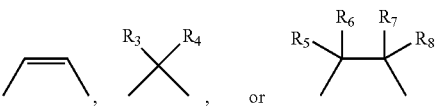

where $R_3$, $R_4$, $R_5$, $R_6$, $R_7$, and $R_8$ are each independently hydrogen or a substituted or unsubstituted $C_1$-$C_{12}$ alkyl group; n, m, j, and k are each independently 0 or 1; and R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

The anthracene derivative compound may be selected from compounds represented by Formulae 3 through 5 below:

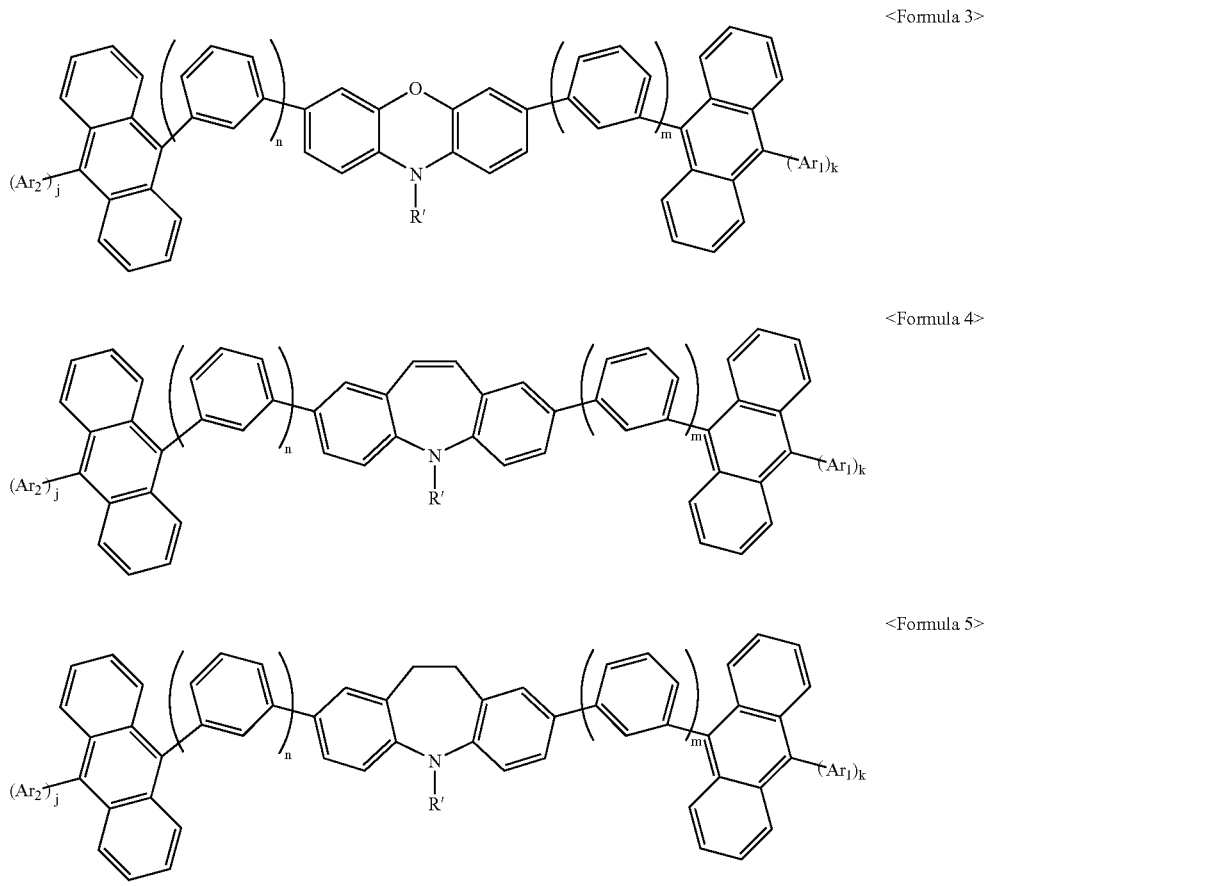

<Formula 3>

<Formula 4>

<Formula 5> wherein, $Ar_1$ and $Ar_2$ are each independently selected from the group consisting of a substituted or unsubstituted $C_5$-$C_{30}$ aryl group, a substituted or unsubstituted $C_1$-$C_{30}$ cycloaryl group, and a substituted or unsubstituted $C_6$-$C_{30}$ arylalkyl group; n, m, j, and k are each independently 0 or 1; and R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

Examples of the unsubstituted alkyl group as used herein include methyl, ethyl, propyl, isobutyl, sec-butyl, tert-butyl, pentyl, iso-amyl, and hexyl. At least one hydrogen atom of the alkyl group may be substituted by a halogen atom, a hydroxy group, a nitro group, a cyano group, a substituted or unsubstituted amino group (—$NH_2$, —$NH(R^a)$, —$N(R^b)(R^c)$ where $R^a$, $R^b$, and $R^c$ are each independently a $C_1$-$C_{10}$ alkyl group), an amidino group, a hydrazine, a hydrazone, a carboxyl group, a sulfonyl group, a phosphonyl group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The aryl group as used herein refers to a carbocyclic aromatic system comprising one or more aromatic rings. The rings may be attached to each other as a pendant group or may be fused. For example, the aryl group may be an aromatic group such as phenyl, naphthyl, or tetrahydronaphthyl. At least one hydrogen atom of the aryl group may be substituted by a halogen atom, a hydroxy group, a nitro group, a cyano group, a substituted or unsubstituted amino group (—$NH_2$, —$NH(R^a)$, —$N(R^b)(R^c)$ where $R^a$, $R^b$, and $R^c$ are each independently a $C_1$-$C_{10}$ alkyl group), an amidino group, hydrazine, hydrazone, a carboxyl group, a sulfonyl group, a phosphonyl group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The term "substituted" as used herein means that any one or more hydrogens on the designated atom or group is replaced with a selection from the indicated group, provided that the designated atom's normal valence is not exceeded. Suitable groups that can be present on a "substituted" position include, but are not limited to, a $C_1$-$C_{12}$ alkyl group, a $C_1$-$C_{12}$ alkoxy group, a halogen atom such as fluorine or chlorine, a $C_1$-$C_{30}$ lower alkylamino group, a hydroxy group, a nitro group, a cyano group, a substituted or unsubstituted amino group (—$NH_2$, —$NH(R^a)$, —$N(R^b)(R^c)$ where $R^a$, $R^b$, and $R^c$ are each independently a $C_1$-$C_{12}$ alkyl group), a carboxyl group, a sulfonyl group, a phosphonyl group, a $C_1$-$C_{20}$ halogenated alkyl group, an alkenyl group, an alkynyl group, a heteroalkyl group, a $C_6$-$C_{30}$ aryl group, an arylalkyl group, a heteroaryl group, and a $C_2$-$C_{30}$ heteroarylalkyl group.

In an exemplary embodiment, the anthracene derivative compound may be selected from compounds represented by Formulae 6 through 11 below, but is not limited thereto:

<Formula 6>
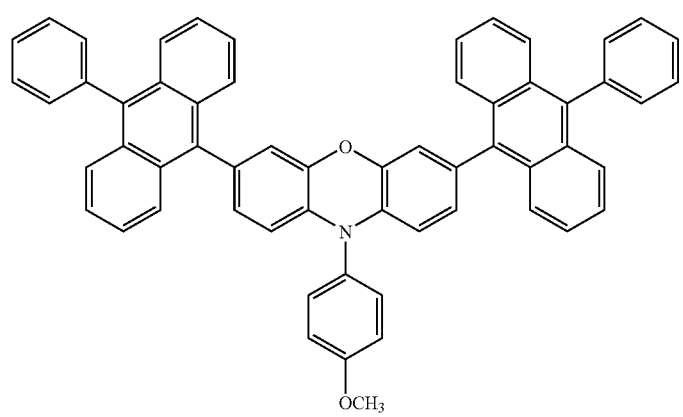
<Formula 7>
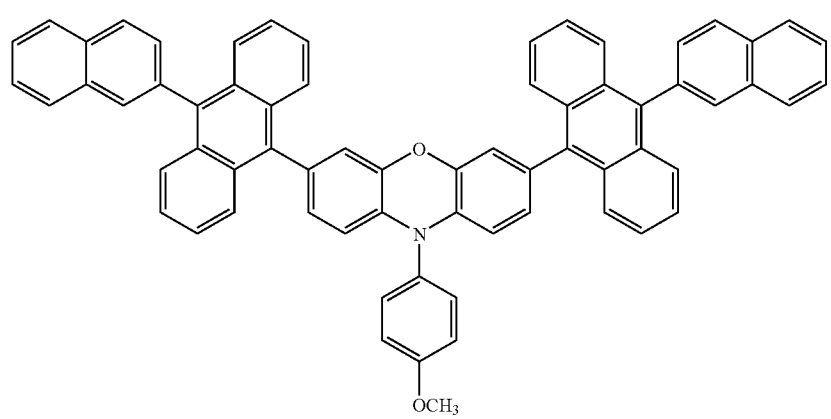
<Formula 8>
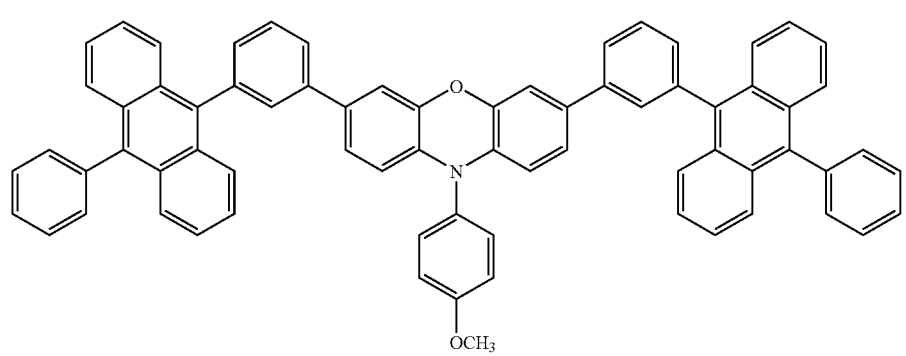
<Formula 9>
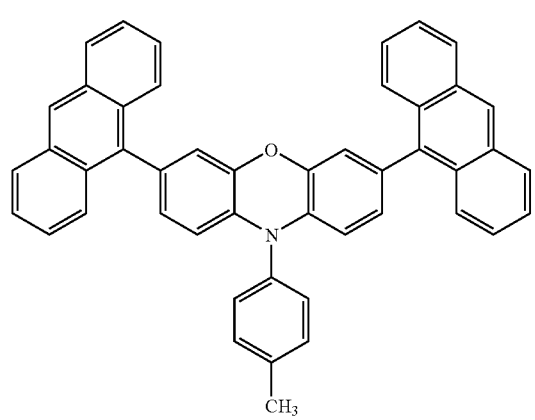
<Formula 10>
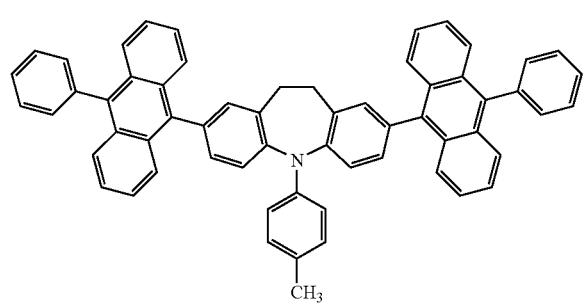

-continued

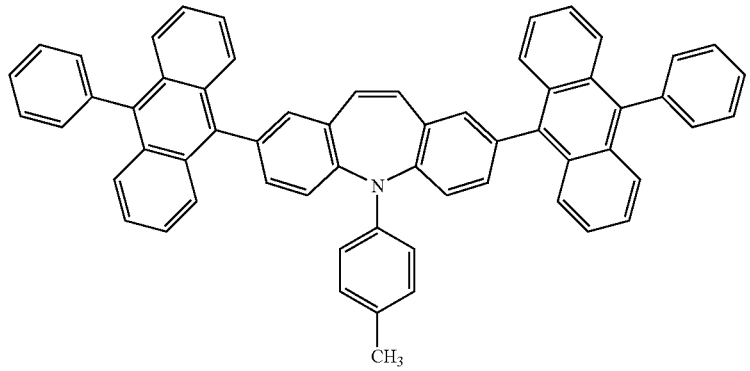

<Formula 11>

Compounds represented by Formula 1 can be synthesized using a conventional synthesis method. Detailed synthesis procedures of these compounds are described in the reaction schemes in the following synthesis examples.

Also provided herein is an OLED comprising: a first electrode; a second electrode; and at least one organic layer interposed between the first electrode and the second electrode, the organic layer comprising an anthracene derivative compound represented by Formula 1.

Specifically, the compound of Formula 1 may be a compound represented by Formula 2 above. More specifically, the compound of Formula 1 may be a compound selected from compounds represented by Formulae 3 through 5 above. Still more specifically, the compound of Formula 1 may be a compound selected from compounds represented by Formulae 6 through 11 above. The anthracene derivative compound is suitable to be used as a host of the organic layer, specifically an emitting layer, and has blue-light emitting characteristics. The emitting layer may further comprise another emitting material.

The OLED can have various structures. At least one selected from the group consisting of a hole injection layer, a hole transport layer, a hole blocking layer, an electron blocking layer, an electron transport layer, and an electron injection layer may be further interposed between the first electrode and the second electrode.

More specifically, FIGS. 1A, 1B, and 1C each illustrate an OLED. Referring to FIG. 1A, an OLED has a stacked structure of first electrode/hole injection layer/hole transport layer/emitting layer/electron transport layer/electron injection layer/second electrode. Referring to FIG. 1B, an OLED has a stacked structure of first electrode/hole transport layer/emitting layer/electron transport layer/electron injection layer/second electrode. Referring to FIG. 1C, an OLED has a stacked structure of first electrode/hole injection layer/hole transport layer/emitting layer/hole blocking layer/electron transport layer/electron injection layer/second electrode. Here, at least one of the emitting layer, the hole injection layer, and the hole transport layer may comprise a compound according to an embodiment of the present invention.

The emitting layer of the OLED may comprise a red, green, blue, or white phosphorescent or fluorescent dopant. The phosphorescent dopant may be an organometallic compound comprising at least one element selected from the group consisting of Ir, Pt, Os, Ti, Zr, Hf, Eu, Tb, and Tm.

Hereinafter, a method of manufacturing an OLED will be described with reference to FIG. 1C.

First, a first electrode material with a high work function is formed on a substrate using deposition or sputtering to form a first electrode. The first electrode may be an anode. Here, the substrate may be a substrate commonly used in OLEDs. Specifically, the substrate may be a glass substrate or a transparent plastic substrate which is excellent in mechanical strength, thermal stability, transparency, surface smoothness, handling property, and water repellency. The first electrode material may be a material with transparency and good conductivity, e.g., indium tin oxide (ITO), indium zinc oxide (IZO), tin oxide ($SnO_2$), or zinc oxide (ZnO).

Next, a hole injection layer (HIL) may be formed on the first electrode using various methods such as vacuum deposition, spin-coating, casting, or the Langmuir-Blodgett (LB) method.

In the case of forming the HIL using a vacuum deposition process, the deposition conditions vary according to the type of the HIL material, the structure and thermal characteristics of the HIL, and the like. However, it is advantageous that the HIL is deposited to a thickness of 10 Å to 5 µm at a deposition rate of 0.01 to 100 Å/sec, at a temperature of 100 to about 500° C., in a vacuum level of $10^{-3}$ to $10^{-3}$ torr.

In the case of forming the HIL using a spin-coating process, the coating conditions vary according to the type of the HIL material, the structure and thermal characteristics of the HIL, and the like. However, it is advantageous that the spin-coating should be performed at a coating speed of about 2,000 to about 5,000 rpm, and, after the spin-coating, a thermal treatment should be performed at a temperature of about 80 to about 200° C. to remove any solvent.

The HIL material may be a compound of Formula 1 or 2 as described above. In addition, the HIL material may be a known hole injection material, such as, a phthalocyanine compound (for example, copper phthalocyanine) disclosed in U.S. Pat. No. 4,356,429, a Starburst-type amine derivative (for example, TCTA, m-MTDATA, or m-MTDAPB) disclosed in *Advanced Material*, 6, p. 677 (1994), or a soluble conductive polymer, such as, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), or polyaniline/poly (4-styrenesulfonate) (PANI/PSS).

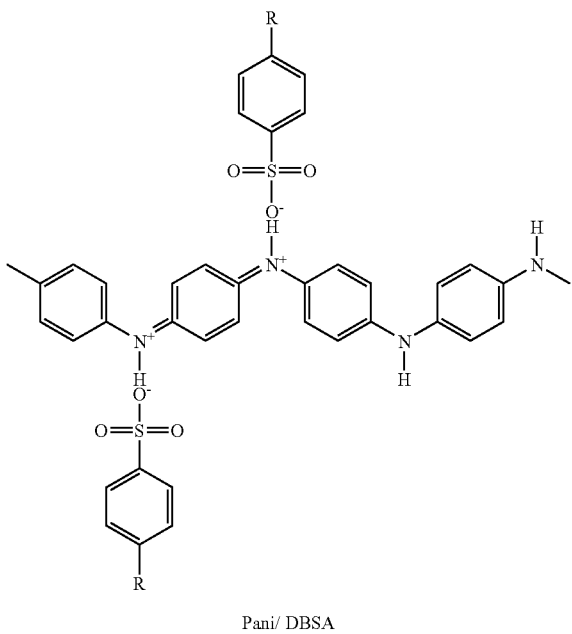

Pani/ DBSA

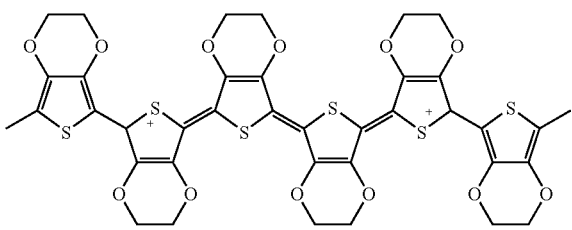

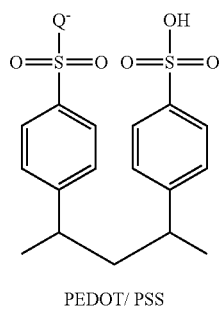

PEDOT/ PSS

The HIL may be formed to a thickness of about 100 to about 10,000 Å, preferably about 100 to about 1,000 Å. If the thickness of the HIL is less than about 100 Å, hole injection characteristics may be adversely affected. On the other hand, if the thickness of the hole injection layer exceeds about 10,000 Å, the driving voltage may be adversely affected.

Next, a hole transport layer (HTL) may be formed on the HIL using various methods such as vacuum deposition, spin-coating, casting, or the LB method. In the case of forming the HTL using vacuum deposition or spin-coating, the deposition or coating conditions vary according to the type of the compound being deposited or coated, but are generally similar to the conditions for the formation of the HIL.

A HTL material may be a compound of Formula 1 as described above. In addition, the hole transport layer material can be a known hole transport material, such as, a carbazole derivative such as N-phenylcarbazole or polyvinylcarbazole; an amine derivative having an aromatic fused ring such as N,N'-bis(3-methylphenyl)-N,N'-diphenyl-[1,1-biphenyl]-4, 4'-diamine (TPD) or N,N'-di(naphthalene-1-yl)-N,N'-diphenylbenzidine (α-NPD); or the like.

The HTL may be formed to a thickness of about 50 to about 1,000 Å, preferably about 100 to about 600 Å. If the thickness of the hole transport layer is less than about 50 Å, hole transport characteristics may be adversely affected. On the other hand, if the thickness of the hole transport layer exceeds about 1,000 Å, the driving voltage may be adversely affected.

Next, an emitting layer (EML) may be formed on the HTL using vacuum deposition, spin-coating, casting, or the LB method. In the case of forming the EML using vacuum deposition or spin-coating, the deposition or coating conditions vary according to the type of the compound being deposited or coated, but are generally similar to the conditions for the formation of the HIL.

The EML may include an anthracene derivative compound of Formula 1 as described above. Here, a known fluorescent host material suitable for the compound of Formula 1 or a known dopant material may also be used. The anthracene derivative compound of Formula 1 may be used as a phosphorescent host alone or in combination with 4,4'-N,N'-dicarbazole-biphenyl (CBP), poly(n-vinylcarbazole) (PVK), or the like. As a phosphorescent dopant, there may be used a red phosphorescent dopant (such as, PtOEP, RD 61 (UDC)), a green phosphorescent dopant (such as, Ir(PPy)$_3$ (PPy=2-phenylpyridine)), or a blue phosphorescent dopant (such as, F2Irpic).

When the anthracene derivative compound of Formula 1 is used as a single host, the doping concentration of a dopant is not limited. Generally, the content of the dopant is about 0.01 to about 15 parts by weight based on 100 parts by weight of the host. On the other hand, when the anthracene derivative compound of Formula 1 is used as a host in combination with another host, the content of the compound of Formula 1 is about 30 to about 99 parts by weight based on the total weight (100 parts by weight) of the hosts.

The EML may be formed to a thickness of about 100 to about 1,000 Å, preferably about 200 to about 600 Å. If the thickness of the EML is less than about 100 Å, emission characteristics may be adversely affected. On the other hand, if the thickness of the emitting layer exceeds about 1,000 Å, the driving voltage may be adversely affected.

In the case where the EML comprises a phosphorescent dopant, a hole blocking layer (HBL) may be formed on the EML using vacuum deposition, spin-coating, casting, or the LB method, in order to prevent the diffusion of triplet excitons or holes into an electron transport layer. In the case of forming the HBL using vacuum deposition or spin coating, the deposition or coating conditions vary according to the type the compound being deposited or coated, but are generally similar to the conditions for the formation of the HIL. An available hole blocking material may be an oxadiazole derivative, a triazole derivative, a phenanthroline derivative, BCP, an aluminum complex, or the like.

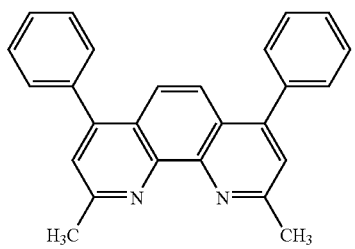

Phenanthroline-containing organic compound

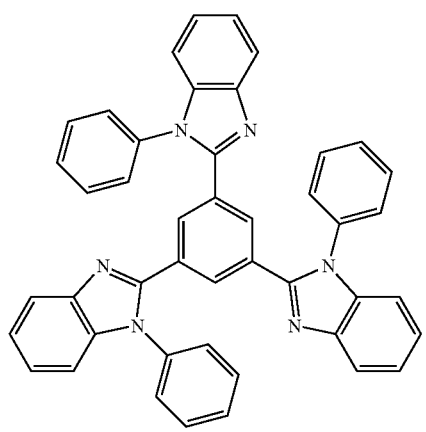

Imidazole-containing organic compound

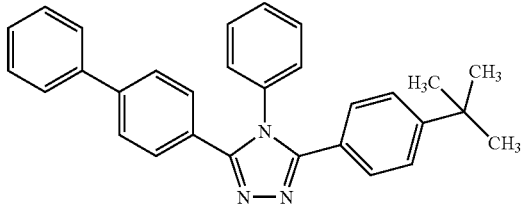

Triazole-containing organic compound

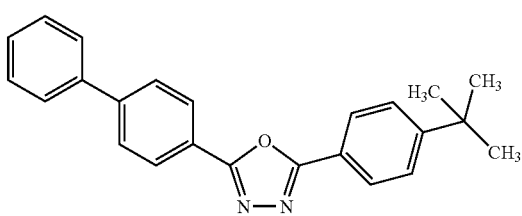

Oxadiazole-containing organic compound

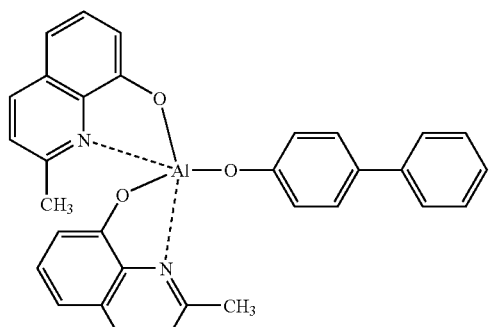

BAlq

The HBL may be formed to a thickness of about 50 to about 1,000 Å, preferably about 100 to about 300 Å. If the thickness of the HBL is less than about 50 Å, hole blocking characteristics may be adversely affected. On the other hand, if the thickness of the HBL exceeds about 1,000 Å, the driving voltage may be adversely affected.

Next, an electron transport layer (ETL) may be formed using various methods such as vacuum deposition, spin-coating, or casting. In the case of forming the electron transport layer using vacuum deposition or spin-coating, the deposition or coating conditions vary according to the type of the compound being coated or deposited, but are generally similar to the conditions for the formation of the HIL. The ETL material serves to stably transport electrons from an electron donor electrode (a cathode) and may be a known material such as an oxazole-based compound, an isoxazole-based compound, a triazole-based compound, an isothiazole-based compound, an oxadiazole-based compound, a thiadiazole-based compound, a perylene-based compound, an aluminum complex (for example, Alq3 (tris(8-quinolinolato)-aluminum), BAlq, SAlq, or Almq3), a gallium complex (for example, Gaq'2OPiv, Gaq'2OAc, 2(Gaq'2)), or the like.

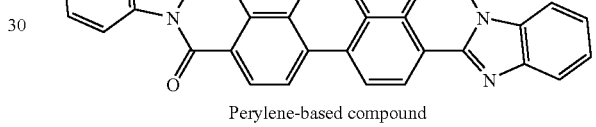

Perylene-based compound

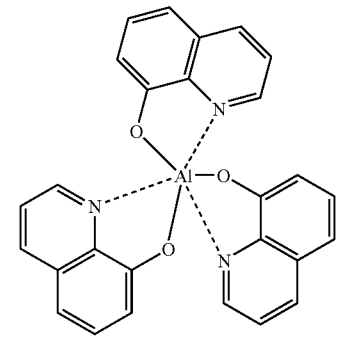

Alq3

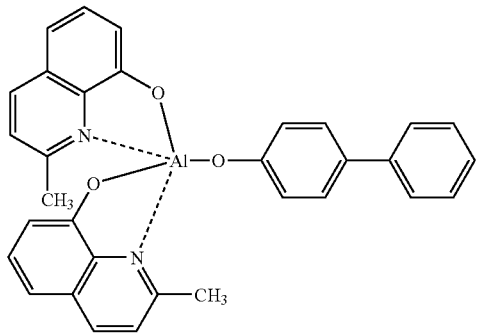

BAlq

-continued

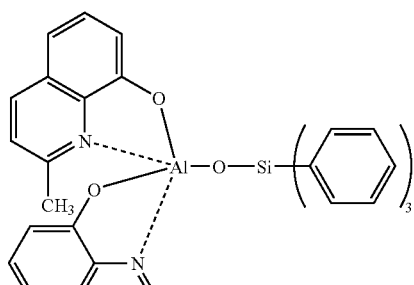
SAlq

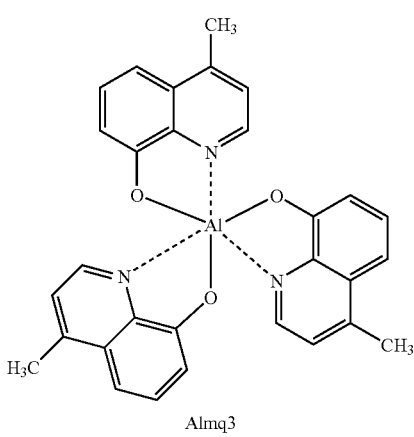
Almq3

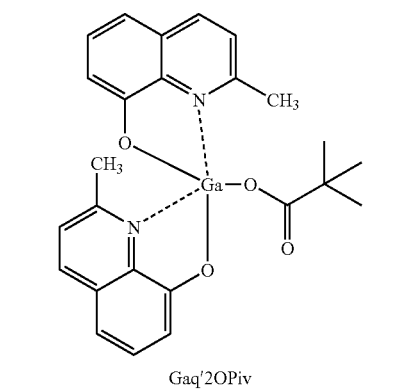
Gaq'2OPiv

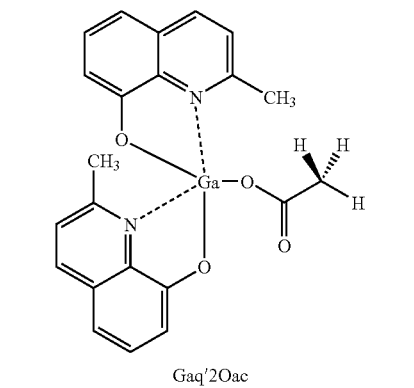
Gaq'2Oac

-continued

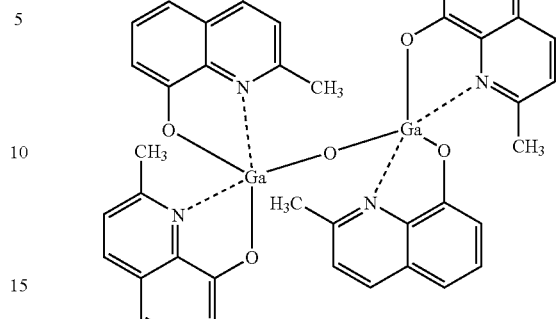
2(Gaq'2)

The ETL may be formed to a thickness of about 100 to about 1,000 Å, preferably about 200 to about 500 Å. If the thickness of the electron transport layer is less than about 100 Å, electron transport characteristics may be adversely affected. On the other hand, if the thickness of the electron transport layer exceeds about 1,000 Å, the driving voltage may be adversely affected.

An electron injection layer (EIL) may be formed on the electron transport layer in order to facilitate the injection of electrons from a cathode. There are no limits as to the material used to form the EIL.

The EIL material may be optionally selected from known materials such as lithium fluoride (LiF), sodium chloride (NaCl), cesium fluoride (CsF), lithium oxide ($Li_2O$), or barium oxide (BaO). The deposition conditions of the EIL vary according to the compound being deposited, but are generally similar to the conditions for the formation of the HIL.

The EIL may be formed to a thickness of about 1 to about 100 Å, preferably about 5 to about 50 Å. If the thickness of the electron injection layer is less than about 1 Å, electron injection characteristics may be adversely affected. On the other hand, if the thickness of the electron injection layer exceeds about 100 Å, the driving voltage may be adversely affected.

Finally, a second electrode may be formed on the EIL using vacuum deposition or sputtering. The second electrode may be used as a cathode. The material for forming the second electrode may be a metal or an alloy with a low work function, an electroconductive compound, or a mixture thereof. For example, the second electrode material may be lithium (Li), magnesium (Mg), aluminum (Al), aluminum-lithium (Al—Li), calcium (Ca), magnesium-indium (Mg—In), magnesium-silver (Mg—Ag), or the like, or a mixture thereof. The second electrode may also be a transmissive cathode formed of ITO or IZO to provide a front-emission type device.

Hereinafter, the present invention will be described more specifically with reference to the following working examples. However, the following working examples are only for illustrative purposes and are not intended to limit the scope of the invention.

Synthesis Example 1

Synthesis of Intermediate A

An intermediate A was synthesized according to Reaction Scheme 1 below:

Reaction Scheme 1

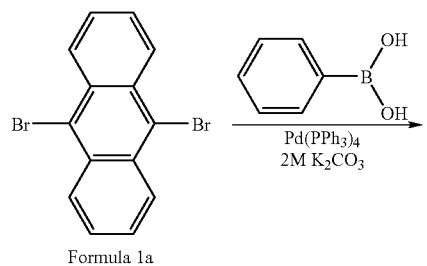

Formula 1a

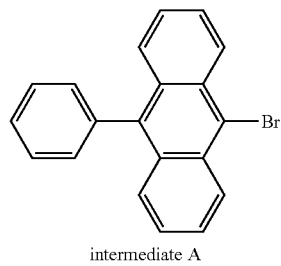

intermediate A 9,10-dibromoanthracene (4.00 g, 11.90 mmol) and phenylboronic acid (1.60 g, 13.12 mmol) were dissolved in toluene (100 ml), and Pd(PPh$_3$)$_4$ (0.68 g, 0.59 mmol) and 2M K$_2$CO$_3$ (24 ml) were gradually dropwise added thereto. The reaction mixture was refluxed for 48 hours and cooled to room temperature. The solvent was removed under reduced pressure, and the residue was extracted with chloroform. The extracted solution was twice washed with a supersaturated sodium chloride solution and water (H$_2$O), and the organic layer was collected and dried over anhydrous magnesium sulfate. The solvent was evaporated to obtain a crude product, and the crude product was purified by silica gel column chromatography to yield 2.27 g (57%) of the intermediate A.

Synthesis Example 2

Synthesis of Intermediate B

An intermediate B,

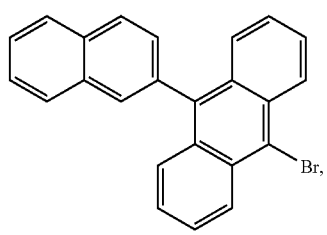

was synthesized according to Synthesis Example 1 except that

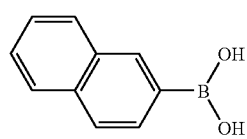

was used instead of

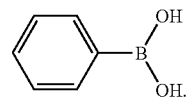

Synthesis Example 3

Synthesis of Intermediate C

An intermediate C was synthesized according to Reaction Scheme 2 below:

Reaction Scheme 2

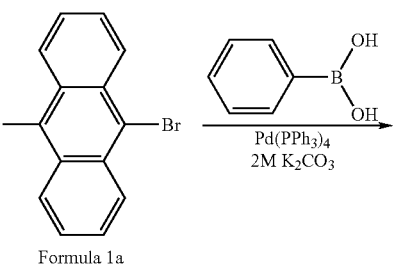

Formula 1a

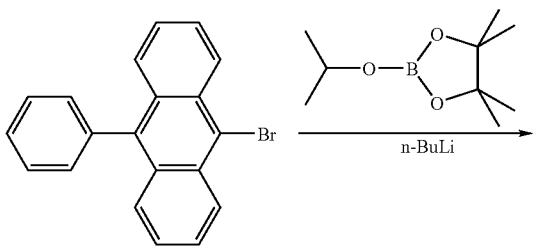

intermediate A

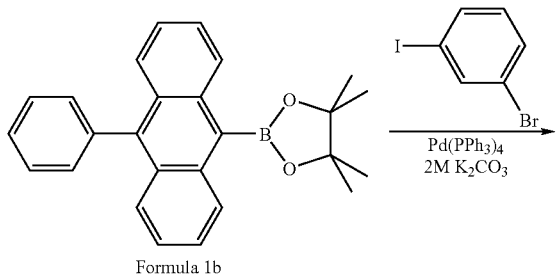

Formula 1b

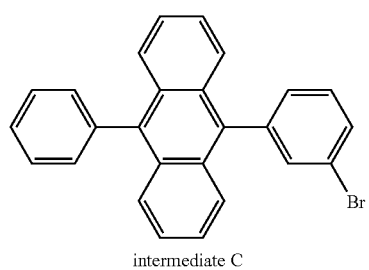

intermediate C

The intermediate A was synthesized according to Synthesis Example 1. The intermediate A (2.20 g, 6.60 mmol) was dissolved in tetrahydrofuran (100 ml), and n-butyllithium (4.6 ml, 7.36 mmol, 1.6 M solution) and 2-isopropoxy-4,4,5,5-tetramethyl-1,3,2-dioxaborolane (1.48 ml, 7.25 mmol) were gradually dropwise added thereto at −78° C. The reaction mixture was heated to room temperature and incubated at room temperature for 15 hours. The reaction was terminated by the addition of water (H₂O) (50 ml), and the resultant solution was extracted with chloroform. The extracted solution was twice washed with a supersaturated sodium chloride solution and water (H₂O), and the organic layer was collected and dried over anhydrous magnesium sulfate. The solvent was evaporated to obtain a crude product, and the crude product was purified by silica gel column chromatography to yield 1.53 g (61%) of the compound of Formula 1b. The intermediate C (1.80 g, yield: 61%) was synthesized according to Synthesis Example 1 except that 3-bromoiodobenzene was used instead of 9,10-dibromoanthracene, and the compound of Formula 1b (2.75 g, 7.23 mmol) was used instead of phenylboronic acid.

Synthesis Example 4

Synthesis of Intermediate D

An intermediate D was synthesized according to Reaction Scheme 3 below:

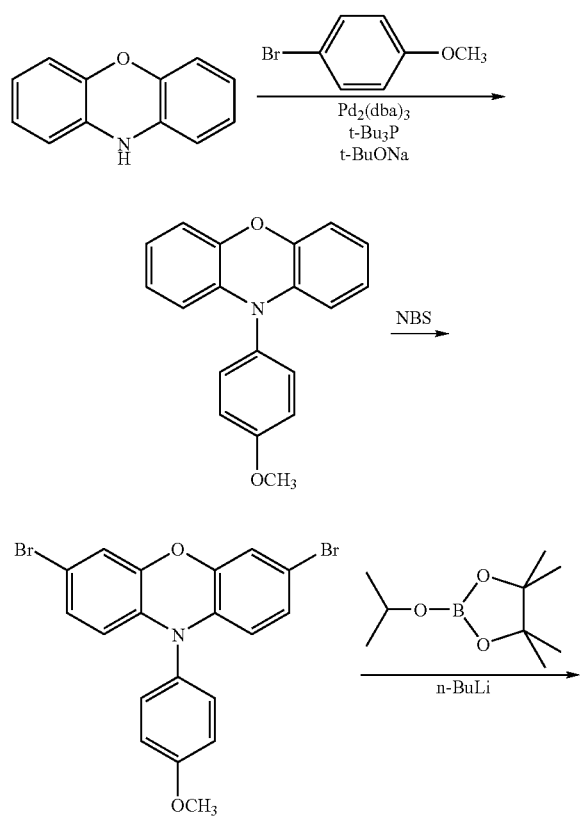

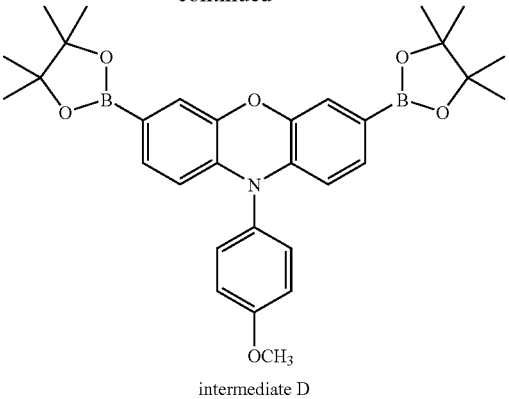

intermediate D

Phenoxazine (2.00 g, 10.92 mmol), 4-bromoanisole (2.25 g, 12.03 mmol), Pd₂(dba)₃ (0.10 g, 0.11 mmol), t-Bu₃P (0.067 g, 0.33 mmol), and t-BuONa (1.57 g, 16.34 mmol) were dissolved in toluene (100 ml), and the reaction mixture was refluxed for 15 hours and cooled to room temperature. The solvent was removed under reduced pressure, and the residue was extracted with chloroform. The extracted solution was twice washed with a supersaturated sodium chloride solution and water (H₂O), and the organic layer was collected and dried over anhydrous magnesium sulfate. The solvent was evaporated to obtain a crude product, and the crude product was purified by silica gel column chromatography to yield 2.27 g (72%) of a compound where the N-position of phenoxazine was substituted by anisole. The compound (2.00 g, 6.91 mmol) was dissolved in chloroform (100 ml), and acetic acid (100 ml) was added thereto. N-bromosuccinimide (NBS) (2.70 g, 15.20 mmol) was added in small amounts at 0° C., and the reaction mixture was heated to room temperature and incubated at room temperature for 10 hours. After the reaction was terminated, the solvent was removed under reduced pressure, and the residue was extracted with chloroform. The extracted solution was twice washed with a supersaturated sodium chloride solution and water (H₂O), and the organic layer was collected and dried over anhydrous magnesium sulfate. The solvent was evaporated to obtain a crude product, and the crude product was purified by silica gel column chromatography to yield 2.62 g (85%) of a phenoxazine derivative compound substituted by a dibromo compound. The phenoxazine derivative compound (1.47 g, 3.29 mmol) was dissolved in tetrahydrofuran (100 ml), and n-butyllithium (4.6 ml, 7.36 mmol, 1.6 M solution) and 2-isopropoxy-4,4,5,5-tetramethyl-1,3,2-dioxaborolane (1.48 ml, 7.25 mmol) were gradually dropwise added thereto at −78° C. The reaction mixture was gradually heated to room temperature and incubated at room temperature for 15 hours. The reaction was terminated by the addition of water (H₂O) (50 ml), and the resultant solution was extracted with chloroform. The extracted solution was twice washed with a supersaturated sodium chloride solution and water (H₂O), and the organic layer was collected and dried over anhydrous magnesium sulfate. The solvent was evaporated to obtain a crude product, and the crude product was purified by silica gel column chromatography to yield 1.16 g (65%) of the intermediate D.

Synthesis Example 5

Synthesis of Compound of Formula 6

<Reaction Scheme 4>

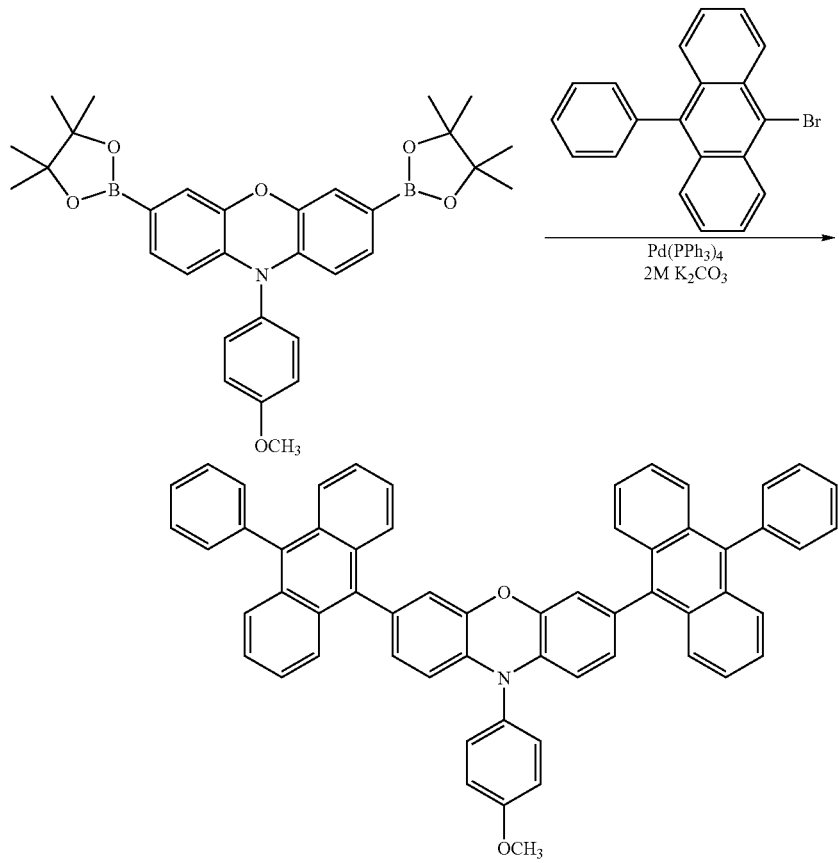

The intermediate D (2.50 g, 4.62 mmol) and the intermediate A (4.63 g, 13.89 mmol) were dissolved in toluene (100 ml), and Pd(PPh$_3$)$_4$ (0.54 g, 0.67 mmol) and 2M K$_2$CO$_3$ (13 ml) were gradually dropwise added thereto. The reaction mixture was refluxed for 48 hours and cooled to room temperature. The solvent was removed under reduced pressure, and the residue was extracted with chloroform. The extracted solution was twice washed with a supersaturated sodium chloride solution and water (H$_2$O), and the organic layer was collected and dried over anhydrous magnesium sulfate. The solvent was evaporated to obtain a crude product, and the crude product was purified by silica gel column chromatography to yield 2.24 g (61%) of a compound of Formula 6.

Synthesis Example 6

Synthesis of Compound of Formula 7

<Reaction Scheme 5>

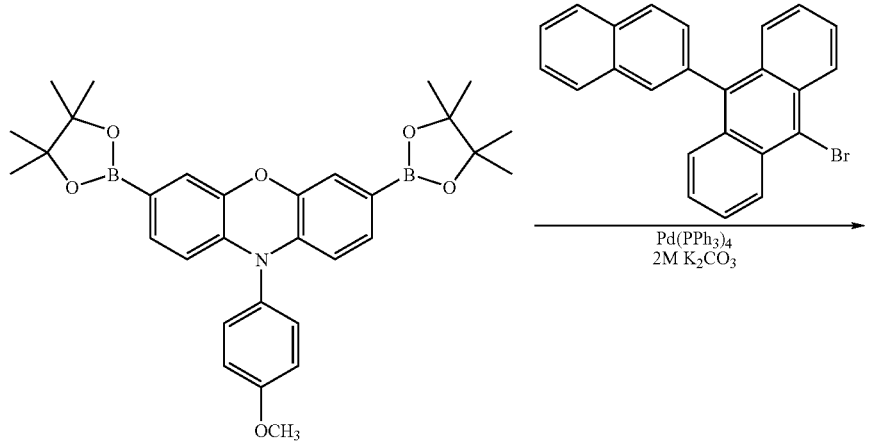

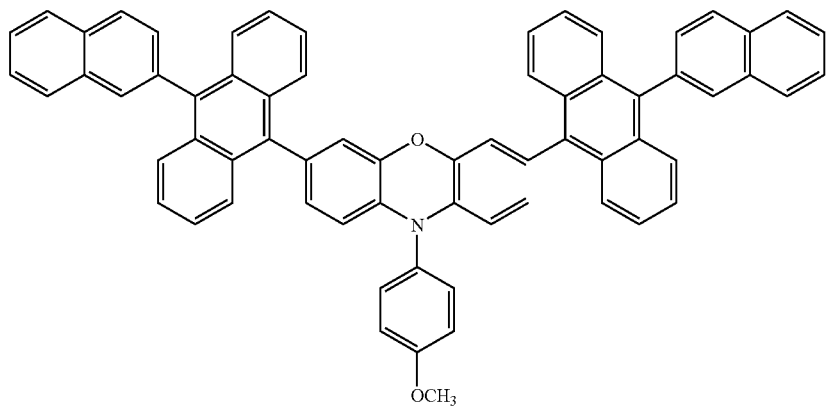
2.35 g (yield: 57%) of a compound of Formula 7 was synthesized according to Synthesis Example 5 except that the intermediate B was used instead of the intermediate A.
Synthesis Example 7
Synthesis of Compound of Formula 8
<Reaction Scheme 6>
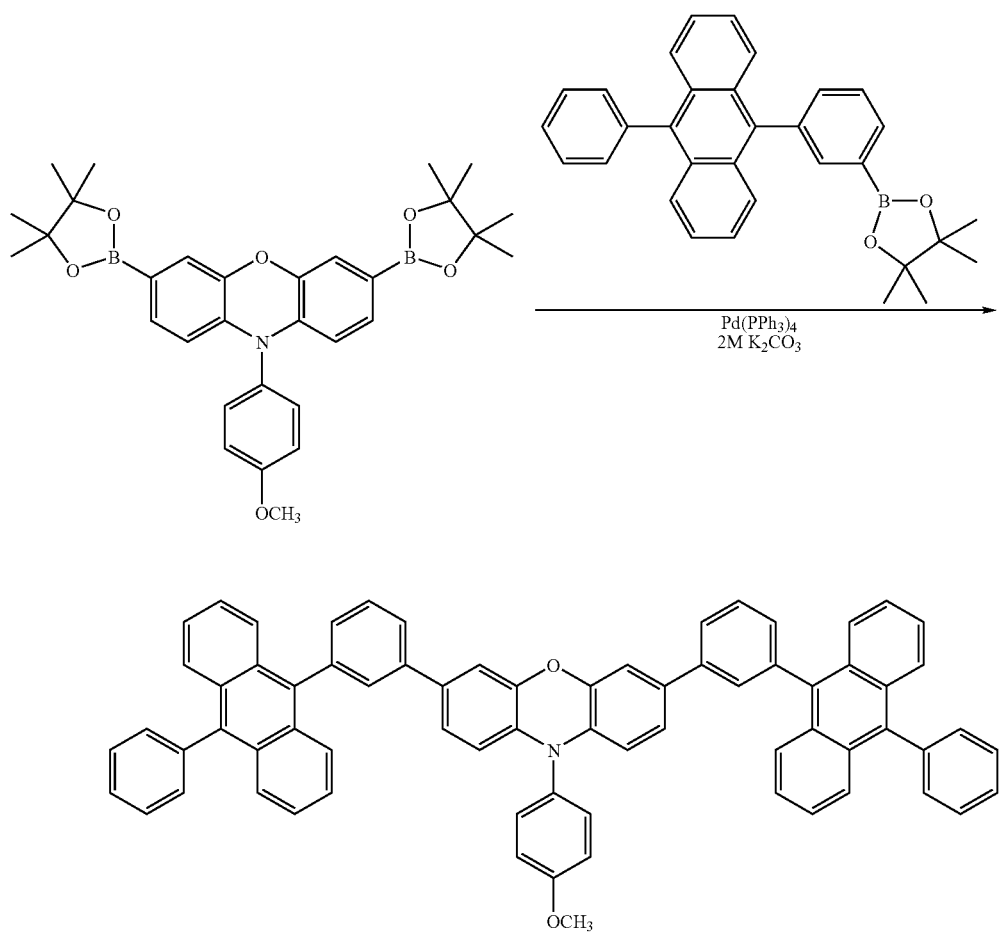

2.23 g (yield: 51%) of a compound of Formula 8 was synthesized according to Synthesis Example 5 except that the intermediate C was used instead of the intermediate A.

Synthesis Example 8

Synthesis of Compound of Formula 9

<Reaction Scheme 7>

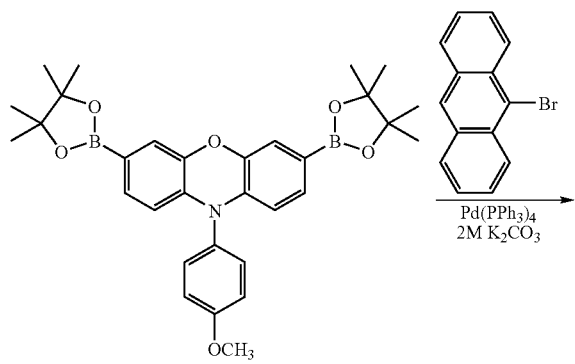

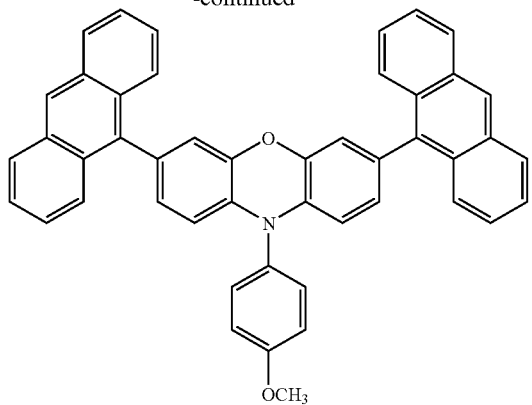

2.05 g (yield: 71%) of a compound of Formula 9 was synthesized according to Synthesis Example 5 except that 9-bromoanthracene was used instead of the intermediate A.

Synthesis Example 9

Synthesis of Compound of Formula 10

<Reaction Scheme 8>

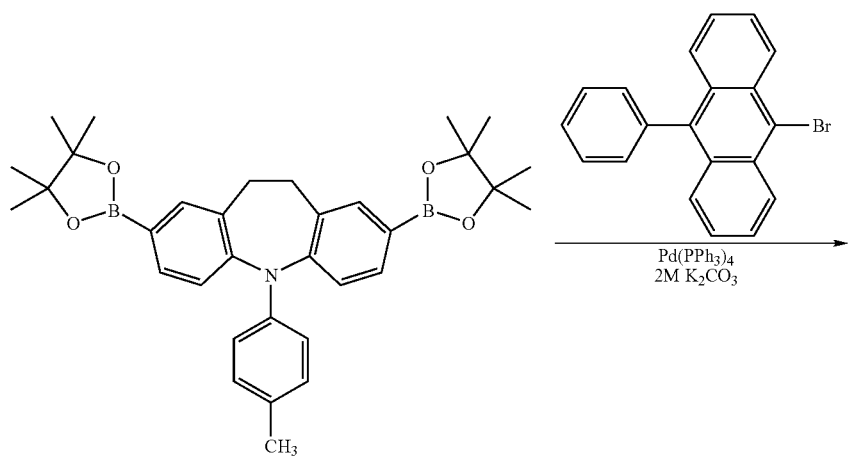

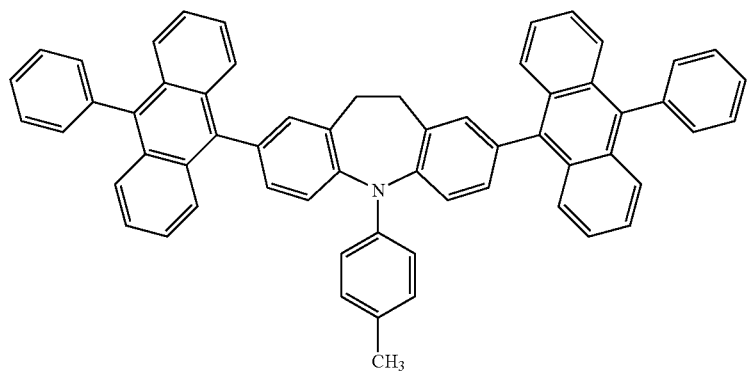

1.90 g (yield: 52%) of a compound of Formula 10 was synthesized using the intermediate A according to Synthesis Example 5 except that the starting material of Reaction Scheme 8 was used instead of the intermediate D.

Synthesis Example 10

Synthesis of Compound of Formula 11

<Reaction Scheme 9>

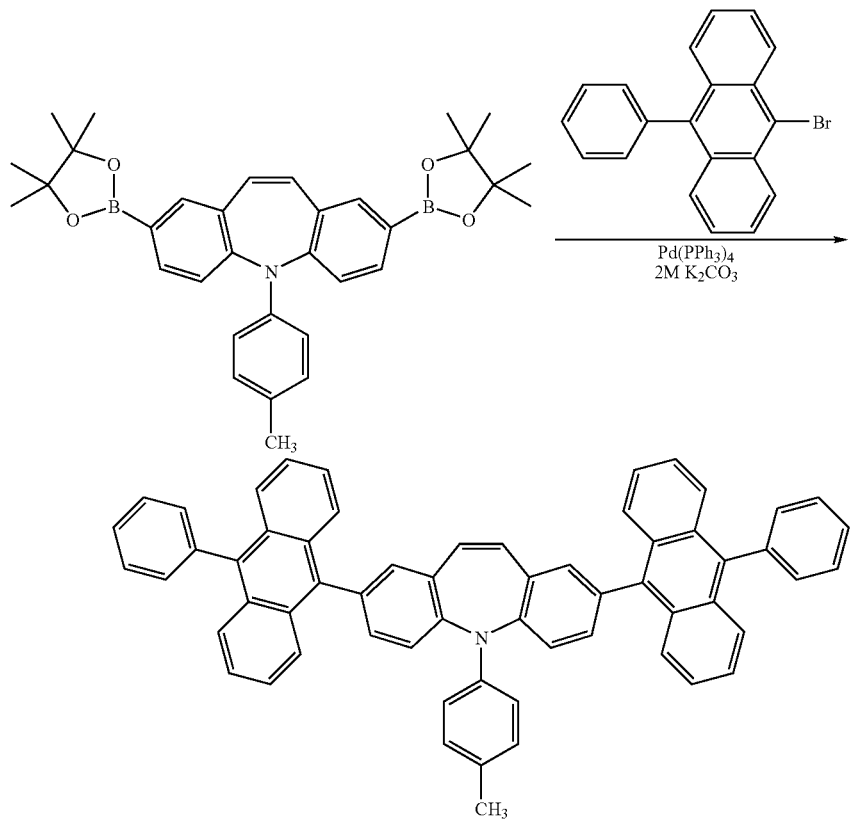

1.75 g (yield: 48%) of a compound of Formula 11 was synthesized using the intermediate A according to Synthesis Example 5 except that the starting material of Reaction Scheme 9 was used instead of the intermediate D.

Evaluation Example 1

Evaluation of Emission Characteristics

The photoluminescence (PL) spectra of the compounds of Formulae 6 through 11 in solution phase and in film phase were measured to evaluate their emission characteristics.

In order to evaluate optical characteristics of the solution phase, the compound of Formula 6 was diluted with toluene to a concentration of 10 mM, and the PL spectrum of the diluted solution was measured using an ISC PC1 spectrofluorometer equipped with a xenon lamp. The same experiment was performed for the compounds of Formulae 7 through 11. The results are presented in Table 1 below.

On the other hand, in order to evaluate optical characteristics of the film phase, quartz substrates were prepared and washed with acetone and pure water. The compound of Formula 6 was spin-coated on the substrates and heated at 110° C. for 30 minutes to form films with a thickness of 1,000 Å. The PL spectra of the films were measured. The same experiment was performed for the compounds of Formulae 7 through 11. The results are presented in Table 2 below.

TABLE 1

| Compound | Maximum absorption wavelength (nm) | Maximum PL wavelength (nm) |
|---|---|---|
| Formula 6 | 356, 376, 396 | 484 |
| Formula 7 | 357, 377, 397 | 495 |
| Formula 8 | 357, 376, 397 | 415, 442 |
| Formula 9 | 356, 377, 397 | 480 |
| Formula 10 | 357, 377, 397 | 412, 432 |
| Formula 11 | 357, 377, 395 | 485 |

TABLE 2

| Compound | Maximum absorption wavelength (nm) | Maximum PL wavelength (nm) |
|---|---|---|
| Formula 6 | 360, 380, 400 | 495 |
| Formula 7 | 362, 382, 402 | 510 |
| Formula 8 | 361, 380, 401 | 423, 450 |
| Formula 9 | 361, 382, 402 | 491 |
| Formula 10 | 361, 380, 401 | 422, 441 |
| Formula 11 | 362, 382, 403 | 497 |

The results of Tables 1 and 2 show that a compound according to the present invention has emission characteristics suitable to be used in an OLED.

Example 1

OLEDs having the following structure were manufactured using each compound of Formulae 6, 7, 9, and 11 as the host of the EML and DCM2 as the dopant of the EML: ITO(1000 Å)/α-NPD(60 nm)/(each compound of Formulae 6, 7, 9, and 11=99 wt %/DCM2=1 wt %) (30 nm)/Alq3(40 nm)/LiF(1 nm)/Al(200 nm). The structure of DCM2 was as follows.

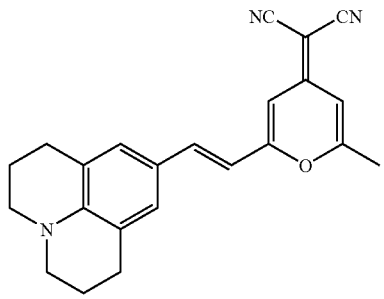

A 15 Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. α-NPD was vacuum-deposited to a thickness of 60 nm on the anodes. A mixture of each compound of Formulae 6, 7, 9, and 11 and DCM2 (weight ratio (%)=99:1) was vacuum-deposited to a thickness of 30 nm to form EMLs. Alq3 was vacuum-deposited to a thickness of 40 nm on the EMLs to form ETLs. LiF (1 nm, EILs) and Al (200 nm, cathodes) were sequentially vacuum-deposited on the ETLs to thereby complete the OLEDs as illustrated in FIG. 1B. The emission characteristics of the devices are summarized in Table 3 below.

Comparative Example 1

OLEDs were manufactured in the same manner as in Example 1 except that Alq3 alone was used as the light-emitting material. The emission characteristics of the devices are summarized in Table 3 below.

TABLE 3

| Compound | Driving voltage (V) | Maximum current efficiency (cd/A) | External quantum efficiency (%) | CIE coordinate (~100 cd/m²) |
| --- | --- | --- | --- | --- |
| Comparative Example 1 (Alq3) | 3.7 | 1.7 | 0.2 | (0.62, 0.38) |
| Formula 6 | 3.2 | 3.9 | 1.8 | (0.58, 0.42) |
| Formula 7 | 3.5 | 3.7 | 1.6 | (0.54, 0.44) |
| Formula 9 | 3.2 | 3.8 | 1.7 | (0.60, 0.40) |
| Formula 11 | 3.3 | 3.7 | 1.5 | (0.61, 0.40) |

Example 2

OLEDs having the following structure were manufactured using each compound of Formulae 8 and 10 as the host of the EML and DPAVBi as the dopant of the EML: ITO(1000 Å)/(M-TDATA)(35 nm)/α-NPD(30 nm)/(each compound of Formulae 8 and 10=95 wt %/DPAVBi=5 wt %) (35 nm)/Alq3 (18 nm)/LiF(0.7 nm)/Al(150 nm).

A 15 Ω/cm² (1,000 Å) ITO glass substrate was cut into pieces of 50 mm×50 mm×0.7 mm in size, followed by ultrasonic cleaning in acetone, isopropyl alcohol, and pure water (15 minutes for each) and then UV/ozone cleaning (30 minutes) to form anodes. M-TDATA was vacuum-deposited to a thickness of 35 nm on the anodes, and α-NPD was vacuum-deposited thereon to a thickness of 30 nm. A mixture of each compound of Formulae 8 and 10 and DPAVBi (weight ratio (%) of 95:5) was vacuum-deposited to a thickness of 35 nm to form EMLs. Alq3 was vacuum-deposited to a thickness of 18 nm on the EMLs to form ETLs. LiF (0.7 nm, EILs) and Al (150 nm, cathodes) were sequentially vacuum-deposited on the ETLs to thereby complete OLEDs as illustrated in FIG. 1B. The emission characteristics of the devices are summarized in Table 4 below.

Comparative Example 2

OLEDs were manufactured in the same manner as in Example 2 except that DPAVBi alone was used as the light-emitting material. The emission characteristics of the devices are summarized in Table 4 below.

TABLE 4

| Compound | Driving voltage (V) | Maximum current efficiency (cd/A) | External quantum efficiency (%) | CIE coordinate (~100 cd/m$^2$) |
|---|---|---|---|---|
| Comparative Example 2 (DPAVBi) | 4.5 | 2.10 | 0.9 | (0.15, 0.23) |
| Formula 8 | 3.8 | 6.06 | 3.8 | (0.15, 0.20) |
| Formula 10 | 3.7 | 6.51 | 4.1 | (0.15, 0.21) |

From the above Examples, it can be seen that a compound according to the present invention constituting an EML of an OLED has good emission characteristics as a phosphorescent or fluorescent material.

A compound of Formula 1 according to the present invention has good solubility, and at the same time, good emission characteristics and thermal stability. Therefore, the use of the compound of Formula 1 is suitable for the production of an OLED having a low driving voltage and good color purity.

What is claimed is:

1. An anthracene derivative compound represented by Formula 1 below:

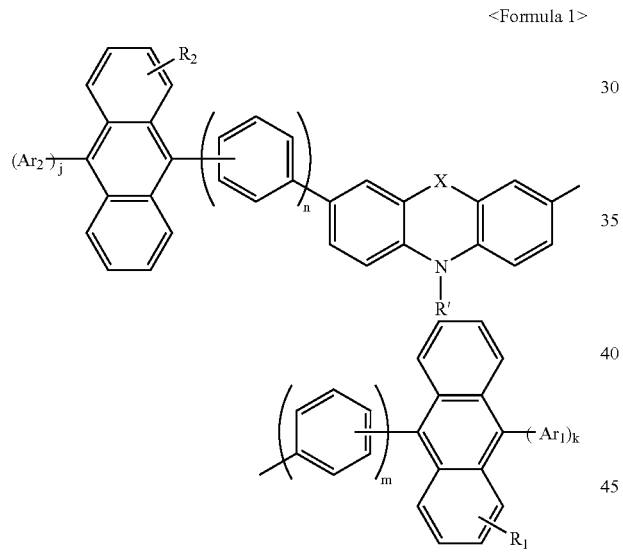

<Formula 1> group, a substituted or unsubstituted $C_1$-$C_{30}$ cycloaryl group, and a substituted or unsubstituted $C_6$-$C_{30}$ arylalkyl group;

X is O,

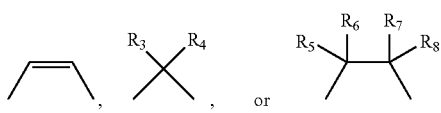

where $R_3$, $R_4$, $R_5$, $R_6$, $R_7$, and $R_8$ are each independently hydrogen or a substituted or unsubstituted $C_1$-$C_{12}$ alkyl group;

n, m, j, and k are each independently 0 or 1;

$R_1$ and $R_2$ are each independently selected from the group consisting of hydrogen, halogen, a cyano group, a hydroxyl group, a substituted or unsubstituted $C_1$-$C_{20}$ alkyl group, a substituted or unsubstituted $C_3$-$C_{20}$ cycloalkyl group, a substituted or unsubstituted $C_5$-$C_{20}$ heterocycloalkyl group, a substituted or unsubstituted $C_1$-$C_{20}$ alkoxy group, a substituted or unsubstituted $C_6$-$C_{20}$ aryl group, a substituted or unsubstituted $C_6$-$C_{20}$ arylalkyl group, and a substituted or unsubstituted $C_2$-$C_{20}$ heteroaryl group; and R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

2. The anthracene derivative compound of claim 1, represented by Formula 2 below:

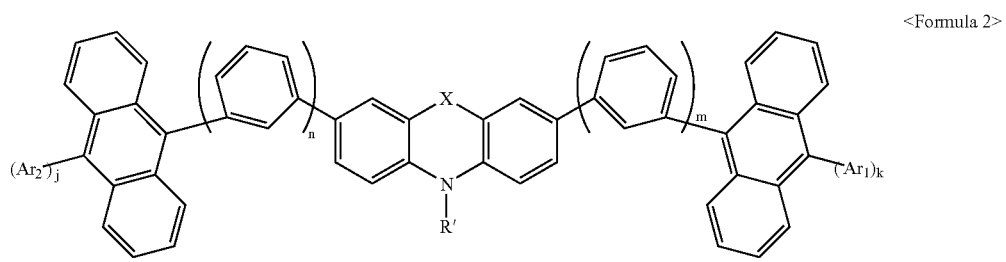

<Formula 2> wherein, $Ar_1$ and $Ar_2$ are each independently selected from the group consisting of a substituted or unsubstituted $C_5$-$C_{30}$ aryl wherein, $Ar_1$ and $Ar_2$ are each independently selected from the group consisting of a substituted or unsubstituted $C_5$-$C_{20}$ aryl group, a substituted or unsubstituted $C_1$-$C_{30}$ cycloaryl group, and a substituted or unsubstituted $C_6$-$C_{30}$ arylalkyl group;

X is O,

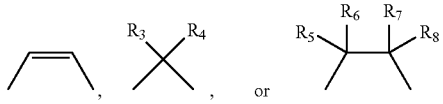

where $R_3$, $R_4$, $R_5$, $R_6$, $R_7$, and $R_8$ are each independently hydrogen or a substituted or unsubstituted $C_1$-$C_{12}$ alkyl group;

n, m, j, and k are each independently 0 or 1; and

R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

3. The anthracene derivative compound of claim 1, represented by Formula 3 below:

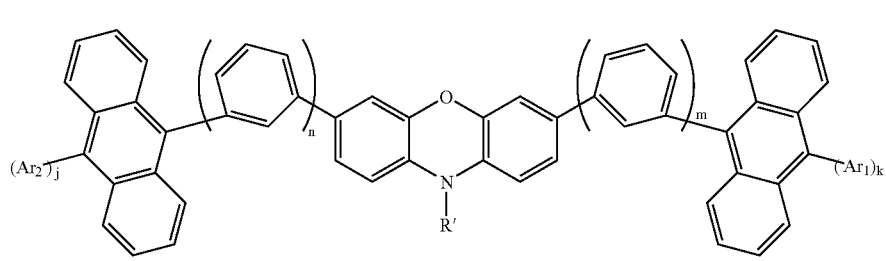

<Formula 3> wherein, $Ar_1$ and $Ar_2$ are each independently selected from the group consisting of a substituted or unsubstituted $C_5$-$C_{30}$ aryl group, a substituted or unsubstituted $C_1$-$C_{30}$ cycloaryl group, and a substituted or unsubstituted $C_6$-$C_{30}$ arylalkyl group;

n, m, j, and k are each independently 0 or 1; and

R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

4. The anthracene derivative compound of claim 1, represented by Formula 4 below:

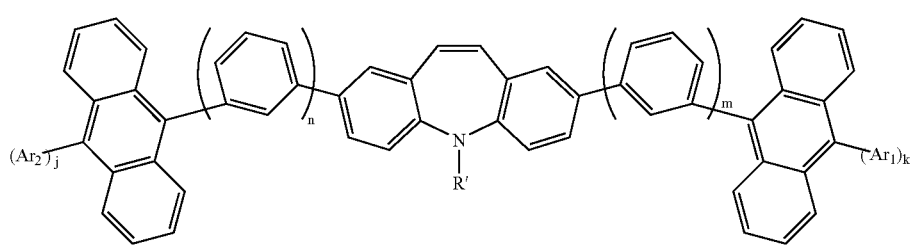

<Formula 4> wherein, $Ar_1$ and $Ar_2$ are each independently selected from the group consisting of a substituted or unsubstituted $C_5$-$C_{30}$ aryl group, a substituted or unsubstituted $C_1$-$C_{30}$ cycloaryl group, and a substituted or unsubstituted $C_6$-$C_{30}$ arylalkyl group;

n, m, j, and k are each independently 0 or 1; and

R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

5. The anthracene derivative compound of claim 1, represented by Formula 5 below:

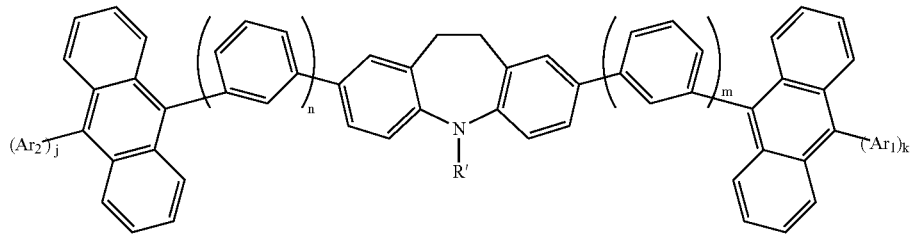
<Formula 5> wherein,
$Ar_1$ and $Ar_2$ are each independently selected from the group consisting of a substituted or unsubstituted $C_5$-$C_{30}$ aryl group, a substituted or unsubstituted $C_1$-$C_{30}$ cycloaryl group, and a substituted or unsubstituted $C_6$-$C_{30}$ arylalkyl group;
n, m, j, and k are each independently 0 or 1; and
R' is a substituted or unsubstituted $C_1$-$C_{20}$ alkyl group, a substituted or unsubstituted $C_3$-$C_{20}$ cycloalkyl group, a substituted or unsubstituted $C_1$-$C_{20}$ alkoxy group, a substituted or unsubstituted $C_6$-$C_{30}$ aryl group, or a substituted or unsubstituted $C_6$-$C_{30}$ aralkyl group.

6. The anthracene derivative compound of claim 1, selected from compounds represented by Formulae 6 through 11 below:

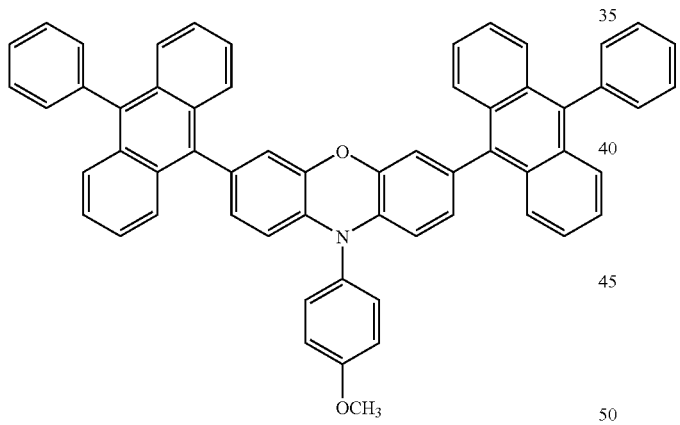
<Formula 6>

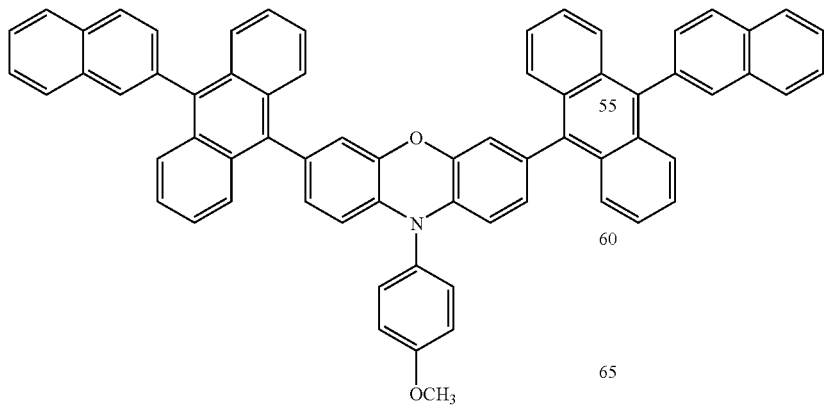
<Formula 7>

-continued

<Formula 8>
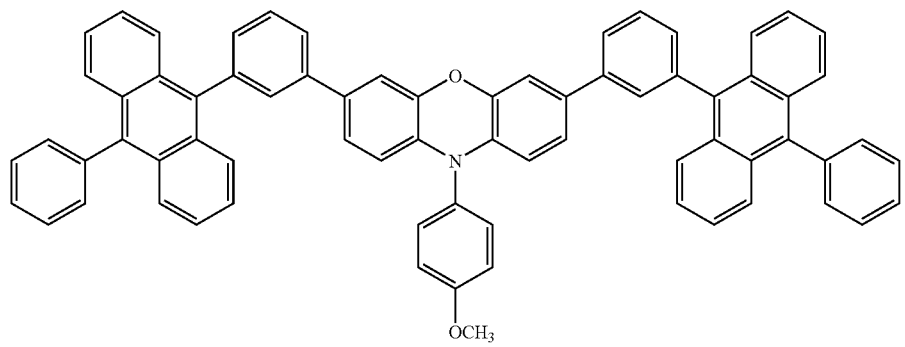

<Formula 9>
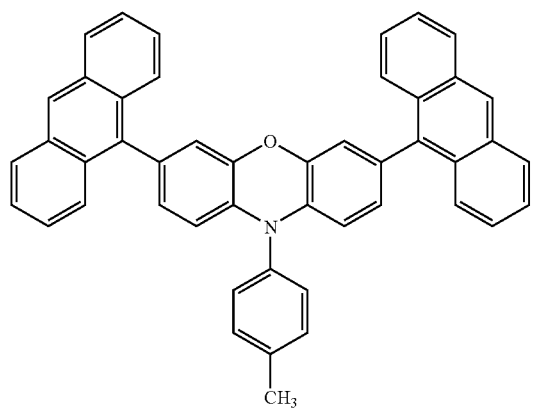

<Formula 10>
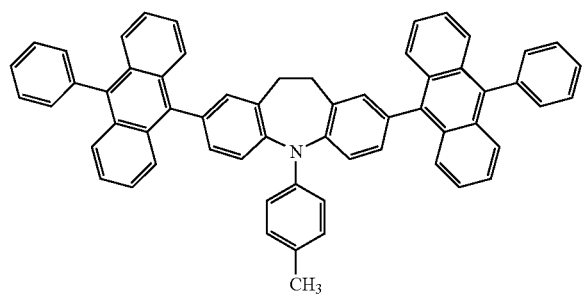

<Formula 11>
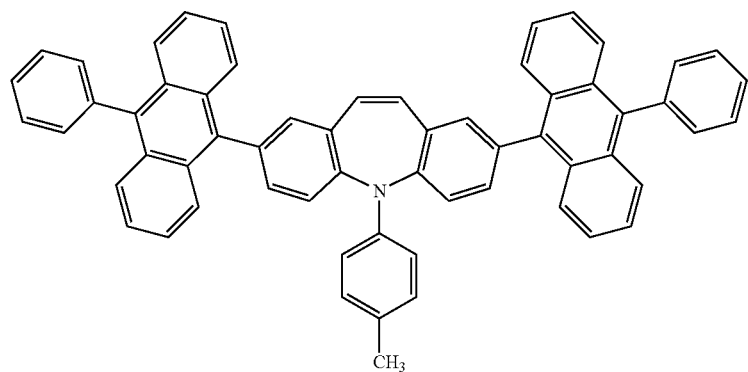

7. An organic light-emitting device comprising:
a first electrode;
a second electrode; and
at least one organic layer interposed between the first electrode and the second electrode, the organic layer comprising the compound of claim 1.

8. The organic light-emitting device of claim 7, wherein the organic layer is an emitting layer.

9. The organic light-emitting device of claim 7, further comprising at least one layer selected from the group consisting of a hole injection layer, a hole transport layer, an electron blocking layer, a hole blocking layer, an electron transport layer, and an electron injection layer, interposed between the first electrode and the second electrode.

10. The organic light-emitting device of claim 9, having the structure of first electrode/hole injection layer/emitting layer/ electron transport layer/electron injection layer/second electrode, first electrode/hole injection layer/hole transport layer/ emitting layer/electron transport layer/electron injection layer/second electrode, or first electrode/hole injection layer/ hole transport layer/emitting layer/hole blocking layer/electron transport layer/electron injection layer/second electrode.

* * * * *